United States Patent
Hersh et al.

(10) Patent No.: US 7,775,987 B2
(45) Date of Patent: Aug. 17, 2010

(54) COMPUTATION OF BLOOD PRESSURE USING DIFFERENT SIGNAL PROCESSING CHANNELS

(75) Inventors: Lawrence T. Hersh, Tampa, FL (US); Sai Kolluri, Tampa, FL (US); Bruce A. Friedman, Tampa, FL (US); Richard Medero, Tampa, FL (US)

(73) Assignee: General Electric Company, Schenectady, NY (US)

( * ) Notice: Subject to any disclaimer, the term of this patent is extended or adjusted under 35 U.S.C. 154(b) by 1304 days.

(21) Appl. No.: 11/284,206

(22) Filed: Nov. 21, 2005

(65) Prior Publication Data
US 2007/0118036 A1    May 24, 2007

(51) Int. Cl.
A61B 5/02    (2006.01)
(52) U.S. Cl. .................. 600/490; 600/485; 600/500
(58) Field of Classification Search .......... 600/485–509
See application file for complete search history.

(56) References Cited

U.S. PATENT DOCUMENTS

| | | | |
|---|---|---|---|
| 4,349,034 A | 9/1982 | Ramsey, III | |
| 4,360,029 A | 11/1982 | Ramsey, III | |
| 4,367,751 A * | 1/1983 | Link et al. | 600/495 |
| 4,543,962 A | 10/1985 | Medero et al. | |
| 4,796,184 A | 1/1989 | Bahr et al. | |
| 4,889,133 A * | 12/1989 | Nelson et al. | 600/494 |
| 4,949,710 A | 8/1990 | Dorsett et al. | |
| 5,590,662 A | 1/1997 | Hersh et al. | |
| 5,704,362 A | 1/1998 | Hersh et al. | |
| 6,358,213 B1 * | 3/2002 | Friedman et al. | 600/493 |
| 2004/0167411 A1 * | 8/2004 | Kolluri et al. | 600/490 |
| 2005/0187483 A1 * | 8/2005 | Kolluri et al. | 600/494 |

* cited by examiner

*Primary Examiner*—Patricia C Mallari
*Assistant Examiner*—Karen E Toth
(74) *Attorney, Agent, or Firm*—Andrus, Sceales, Starke & Sawall, LLP (57) ABSTRACT

A blood pressure measurement system that utilizes a non-invasive blood pressure (NIBP) monitor having a blood pressure cuff and pressure transducer. The measurement system provides a plurality of separate processing techniques that each receive a plurality of oscillometric data values from the pressure transducer. Each of the processing techniques separately constructs an oscillometric envelope based upon the oscillometric data values. Based upon the plurality of separate oscillometric envelopes, the system compares the envelopes and develops a calculated blood pressure from the plurality of envelopes. The calculated blood pressure is then displayed by the NIBP system. The plurality of oscillometric envelopes can be compared and combined in different manners to calculate the patient's blood pressure from the plurality of different processing techniques.

18 Claims, 8 Drawing Sheets

COMPUTATION OF BLOOD PRESSURE USING DIFFERENT SIGNAL PROCESSING CHANNELS

BACKGROUND OF THE INVENTION

The present invention generally relates to automated blood pressure monitoring. More specifically, the present invention relates to automated blood pressure monitors that utilize multiple data processing techniques to process oscillometric data to generate multiple oscillometric waveforms of various properties that can be selected or combined to create a blood pressure measurement that compensates for noise.

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith and incorporated by reference, employs the oscillometric methodology.

In accordance with the Ramsey patents, an inflatable cuff is suitably located on the limb of a patient and is pumped up to a predetermined pressure above the systolic pressure. The cuff pressure is then reduced in predetermined decrements, and at each level, pressure fluctuations are monitored. The resultant arterial pulse signals typically consist of a DC voltage with a small superimposed variational component caused by arterial blood pressure pulsations (referred to herein as "oscillation complexes" or just simply "oscillations").

After suitable filtering to reject the DC component and amplification, peak amplitudes of the oscillations above a given base-line are measured and stored. As the cuff pressure decrementing continues, the peak amplitudes will normally increase from a lower level to a relative maximum, and thereafter will decrease. These amplitudes form an oscillometric envelope for the patient. The lowest cuff pressure at which the oscillations have a maximum value has been found to be representative of the mean arterial pressure (MAP) of the patient. Systolic and diastolic pressures can be derived either as predetermined fractions of the oscillation size at MAP, or by more sophisticated methods of processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on the patient and the operator usually sets a time interval, typically from 1 to 90 minutes, at which blood pressure measurements are to be repeatedly made. The noninvasive blood pressure (NIBP) monitor automatically starts a blood pressure determination at the end of the set time interval.

Figure 1:
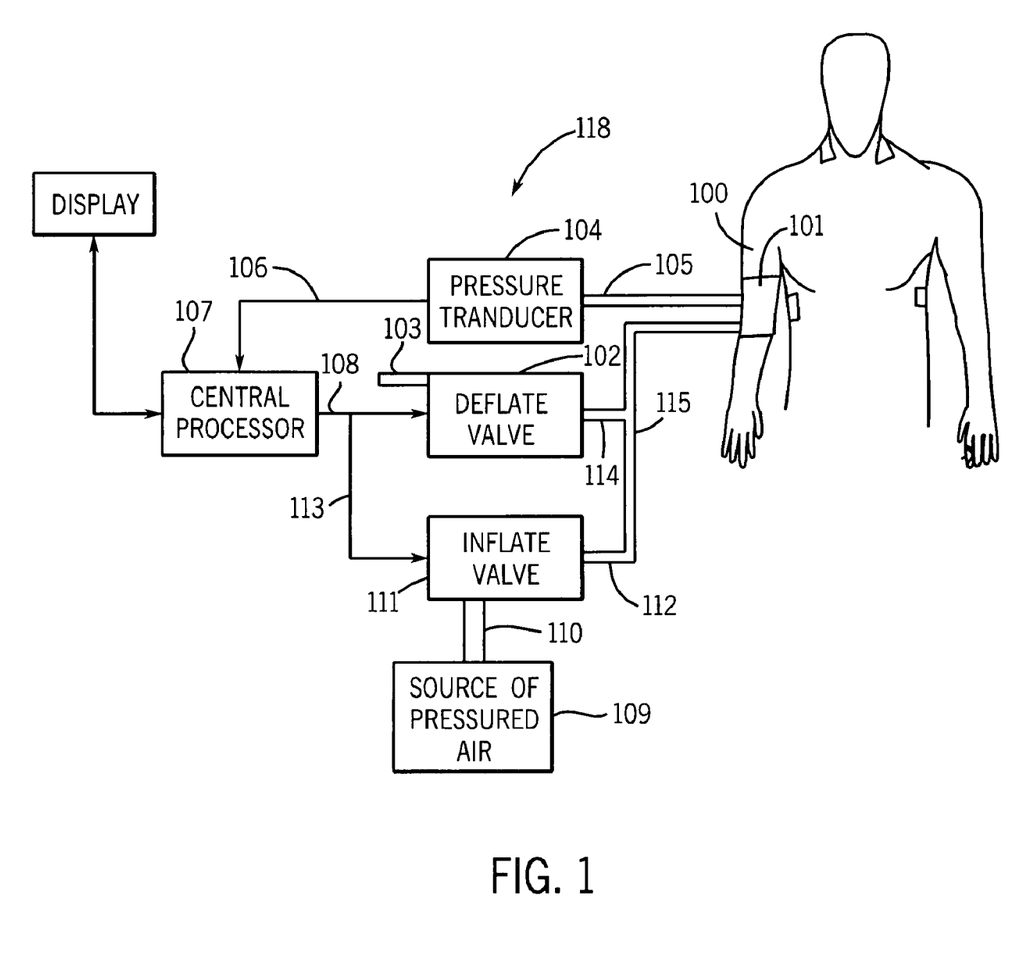
FIG. 1 is a high level diagram of a non-invasive blood pressure (NIBP) monitoring system.

FIG. 1 illustrates a simplified version of the oscillometric blood pressure monitor described in the aforementioned Ramsey patents. In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. The deflation of cuff 101 via deflate valve 102 is controlled by central processor 107 via control line 108.

A pressure transducer 104 is coupled by a duct 105 to the cuff 101 for sensing the pressure therein. In accordance with conventional oscillometric techniques, pressure oscillations in the artery create small pressure changes in the cuff 101, and these pressure oscillations are converted into an electrical signal by transducer 104 and coupled over path 106 to the central processor 107 for processing. In addition, a source of pressurized air 109 is connected via a duct 110 through an inflate valve 111 and a duct 112 to the pressure cuff 101. The inflate valve 111 is electrically controlled through a connection 113 from the central processor 107. Also, the deflate valve 102 is connected by duct 114 via a branch connection 115 with the duct 112 leading to cuff 101.

During operation of the apparatus illustrated in FIG. 1, air under pressure at about 8-10 p.s.i. is typically available as the source of pressurized air 109. When it is desired to initiate a determination of blood pressure, the central processor 107 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Central processor 107 responds to a signal on path 106 from the pressure transducer 104, which is indicative of the instantaneous pressure in the cuff 101, to interrupt the inflation of the cuff 101 when the pressure in the cuff 101 reaches a predetermined initial inflation pressure that is above the estimated systolic pressure of the patient. Such interruption is accomplished by sending a signal over path 113 instructing inflate valve 111 to close. Once inflate valve 111 has been closed, the blood pressure measurement can be obtained by commencing a deflate routine.

Actual measurement of the blood pressure under the control of the central processor 107 using the deflate valve 102 and the pressure transducer 104 can be accomplished in any suitable manner such as that disclosed in the aforementioned patents or as described below. At the completion of each measurement cycle, the deflate valve 102 can be re-opened long enough to relax the cuff pressure via exhaust 103. Thereafter, the deflate valve 102 is closed for the start of a new measurement cycle.

Accordingly, when a blood pressure measurement is desired, the inflate valve 111 is opened while the cuff pressure is monitored using the pressure transducer 104 until the cuff pressure reaches the desired level. The inflate valve 111 is then closed. Thereafter, the deflate valve 102 is operated using signal 108 from microprocessor 107 and the blood pressure measurement taken.

Figure 2:
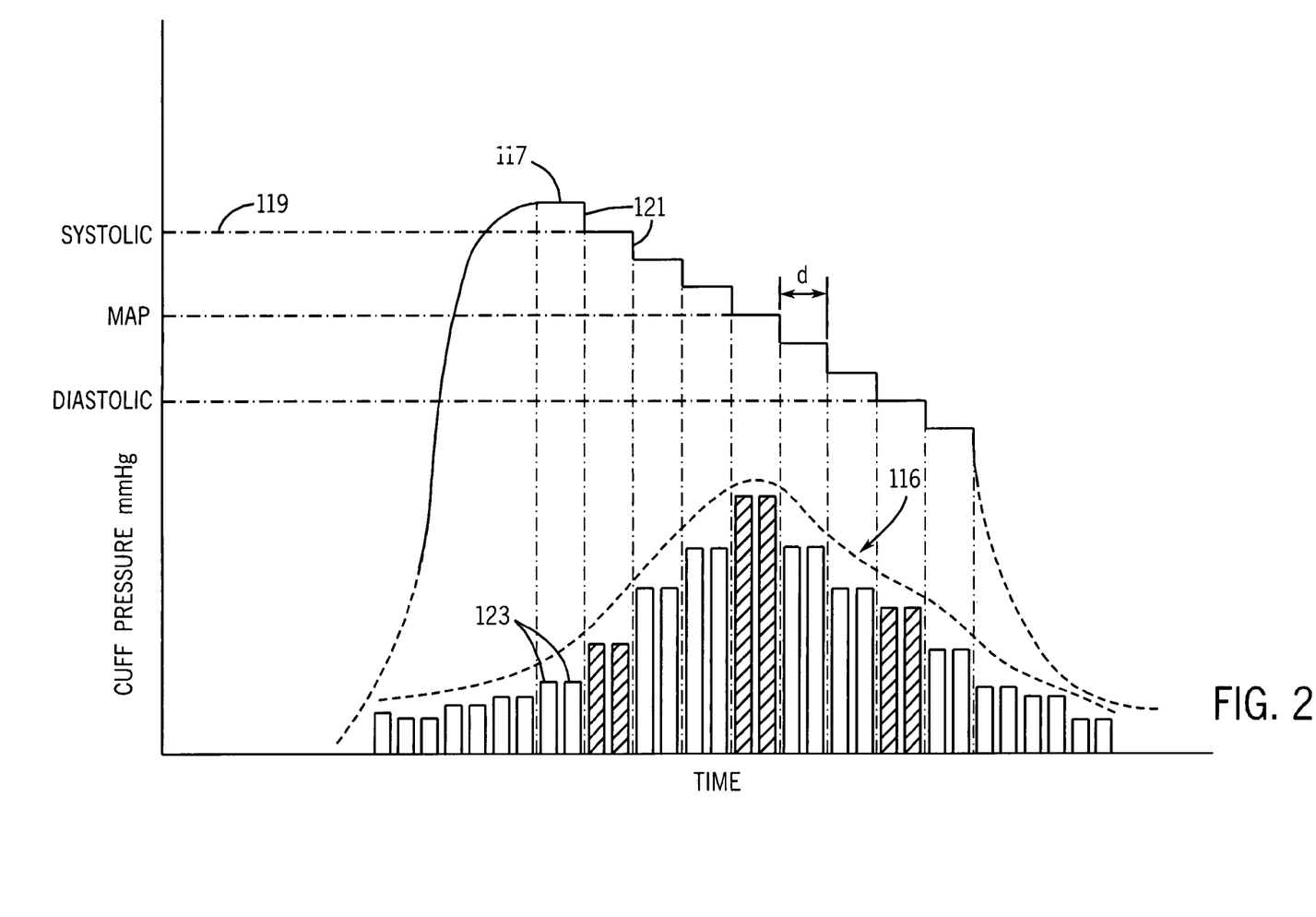
FIG. 2 illustrates oscillometric data including step deflate and oscillation amplitudes derived using the NIBP monitoring system of FIG. 1.

FIG. 2 illustrates a pressure versus time graph illustrating a conventional cuff step deflation and measurement cycle for a conventional NIBP monitor. As illustrated, the cuff is inflated to an initial inflation pressure 117 above the systolic pressure 119, and the cuff is then step deflated by a pressure step 121 to the next pressure level. A timeout duration "d" is provided at each step during which the signal processing circuitry searches for oscillation complexes in accordance with the techniques described in the afore-mentioned commonly assigned patents or as described below. At the end of timeout duration "d", the cuff pressure is decremented even if no oscillation complex is detected. This process of decrementing the pressure and searching for oscillation complexes is repeated until systolic, MAP, and diastolic pressure values can be calculated from the oscillometric envelope 116 data. The entire blood pressure determination process is then repeated at intervals set by the user, some other predetermined interval, or manually.

As shown in FIG. 2, the patient's arterial blood pressure forms an oscillometric envelope 116 comprised of a set of oscillation amplitudes 123 measured at the different cuff pressures. From the oscillometric envelope 116, systolic, MAP and diastolic blood pressures are typically calculated. However, as noted in the afore-mentioned patents, it is desired that all artifact data be rejected from the measured data so that oscillometric envelope 116 contains only the desired amplitude data and no artifacts, thereby improving the accuracy of the blood pressure determinations.

Generally, conventional NIBP monitors of the type described in the afore-mentioned patents use oscillation amplitude matching at each pressure level as one of the ways to discriminate good oscillations from artifacts. In particular, pairs of oscillations are compared at each pressure level to determine if they are similar in amplitude and similar in other attributes, such as shape, area under the oscillation curve, slope, and the like. If the oscillations compare within predetermined limits, the average amplitude and cuff pressure are stored and the pressure cuff is deflated to the next pressure level for another oscillation measurement. However, if the oscillations do not compare favorably, the first oscillation is typically discarded and another fresh oscillation is obtained. The monitor, maintaining the same pressure step, uses this newly obtained oscillation to compare with the one that was previously stored. This process normally continues until two successive oscillations match or a time limit is exceeded.

As discussed above, non-invasive blood pressure algorithms provide a blood pressure value at the end of the determination, which is then displayed to a user. However, during some blood pressure determinations, it is difficult to get data of high enough quality to enable an accurate blood pressure output. As an example, data gathered for the calculation of blood pressure could be corrupted from motion artifacts caused by the patient or by vibrations caused during transport. In the presence of such motion artifacts, signal-processing techniques that are beneficial for handling one type of artifact may not be desirable or may even be detrimental for other types. During the calculation of the blood pressure, it is difficult to determine which processing technique may be best. Therefore, it is desirable to provide a processing technique that utilizes multiple data processing strategies and then judiciously selects the best, resulting in an optimal blood pressure measurement.

SUMMARY OF THE INVENTION

The following describes a method for measuring and displaying the blood pressure of a patient utilizing a non-invasive blood pressure (NIBP) monitor that has an inflatable and deflatable blood pressure cuff and a pressure transducer. The method obtains a series of oscillometric data values from the pressure transducer of the NIBP monitor. The oscillometric data is provided to a central processor that is programmed to carry out various algorithms for processing this measured oscillometric signal for the purpose of calculating blood pressure.

The plurality of oscillometric data values are received in the central processor and the central processor is operated to carry out a plurality of separate, individual processing techniques on the same oscillometric data values. Each of the processing techniques constructs an oscillometric envelope based upon the received oscillometric data values. Since each of the processing techniques is carried out in a different manner, a plurality of potentially different and distinct oscillometric envelopes are calculated by the central processor.

Once the oscillometric envelopes have been developed for each of the processing techniques, the central processor compares the oscillometric envelopes and decides which of the envelopes, or plurality of envelopes, are to be used to calculate the patient's blood pressure. Various techniques can be utilized to process the plurality of oscillometric envelopes calculated by the various processing channels.

One technique of calculating the estimated blood pressure involves comparing each of the oscillometric envelopes from the plurality of filtering channels to a smooth bell curve. This bell curve may have a skew, but is generally nearly Gaussian in character, as is described in U.S. Pat. No. 5,704,362 and is incorporated herein by reference. Based upon the conformance of the oscillometric envelope to a bell curve, a signal quality value is assigned to the oscillometric envelope. After a quality value has been assigned to each of the oscillometric envelopes, the central processor compares the quality value of each of the oscillometric envelopes and selects the oscillometric envelope having the highest signal quality value.

Alternatively, the quality value can be utilized in combination with a distance measurement technique to select one or more of the oscillometric envelopes used to calculate the patient's blood pressure. Specifically, the distance between the blood pressure estimates from each of the oscillometric envelopes are determined and the oscillometric envelopes having the closest distance measurements are selected. If the oscillometric envelopes are of sufficient quality, the oscillometric envelopes that create the closest two measurements can either be averaged or used individually to provide the published-blood pressure.

During the calculation of the patient's blood pressure from the multiple filtering channels, one of the processing techniques can be designated as a priority channel or priority technique. The priority technique is defined as the technique that most often yields high quality results when used with an NIBP monitoring system. During the selection of the oscillometric envelope, the priority channel can be given enhanced weight such that if the quality of the priority channel is sufficient, the priority channel will be selected as the oscillometric envelope for calculation of the blood pressure.

Alternatively, the oscillometric envelopes from each of the processing techniques can be combined, after a normalization scaling, to generate an aggregate oscillometric envelope. The aggregate oscillometric envelope utilizes data points from each of the processing techniques to develop an aggregate, combined oscillometric envelope. Preferably, each of the plurality of oscillometric envelopes are compared to a standard bell shape, and if any of the oscillometric envelopes deviate from the standard expected shape, the data values from that oscillometric envelope are discarded.

By utilizing the method described herein, the central processor can utilize a plurality of processing techniques to eliminate or significantly reduce the effect motion artifacts may have on the calculation of a patient's blood pressure. The combination of the different signal processing techniques allows the techniques to be combined to output the best possible blood pressure values.

BRIEF DESCRIPTION OF THE DRAWINGS

The drawings illustrate the best mode presently contemplated of carrying out the invention. In the drawings.

DETAILED DESCRIPTION OF THE PREFERRED EMBODIMENT

Figure 3:
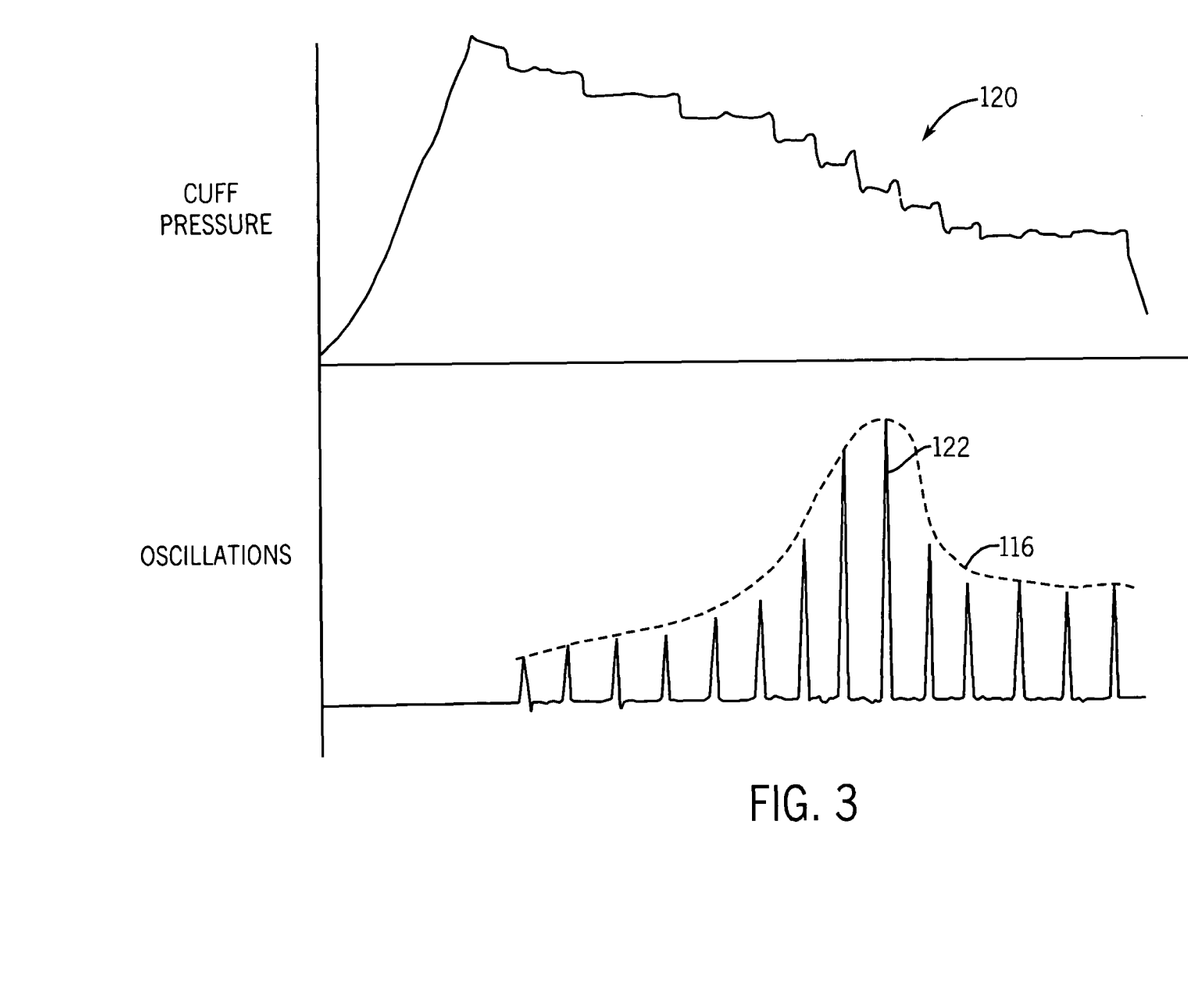
FIG. 3 is an example of an oscillometric blood pressure envelope with high quality, clean data.
Figure 4:
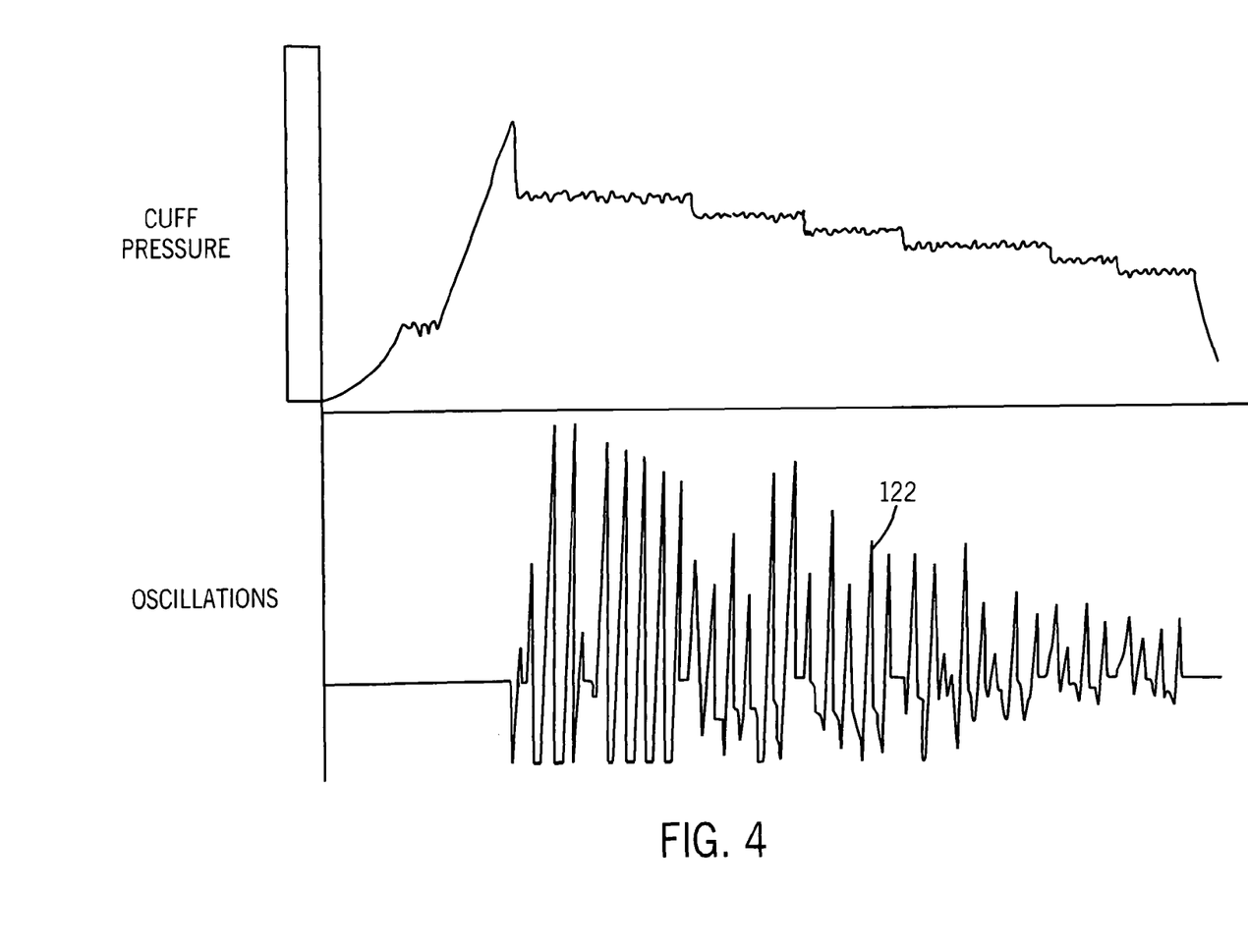
FIG. 4 is an example of an oscillometric blood pressure envelope including step deflate and complexes under artifact-ridden conditions.

As described previously in the description of FIGS. 1 and 2, the NIBP monitoring system 118 generates a cuff pressure deflation profile 120 and a series of oscillometric data values 122 for each pressure step that generally fit close to a bell-shaped envelope 116, as shown in FIG. 3. In the measurement shown in FIG. 3, the oscillometric envelope 116 is created with high quality, clean data as illustrated by the cuff pressure curve 120. Referring now to FIG. 4, thereshown is an example of oscillometric envelope data values under artifact-ridden conditions. With this type of oscillometric data values 122, a single, standard method of determining blood pressure may not be effective due to the artifacts included in the oscillometric data values.

In a typical NIBP monitoring system, such as shown and described in U.S. Pat. No. 6,358,213, the oscillometric data values are filtered using a conventional band pass filter having a lower cutoff frequency near 0.5 Hz and an upper cutoff frequency near 7.2 Hz. Although this band pass filter has proven to be an effective data processing technique for filtering out unwanted noise and artifacts, the band pass may sometimes be ineffective for removing artifacts due to patient motion or transportation.

As described previously, the pressure transducer 104 shown in FIG. 1 generates a series of oscillometric data values for each cuff pressure step, as can be understood in FIGS. 1 and 2. The oscillometric data is a waveform that is fed to the central processor 107 along path 106 for sampling and further processing. The present invention provides for multiple methods of operating the central processor 107 to process the oscillometric data received from the pressure transducer 104.

Figure 5:
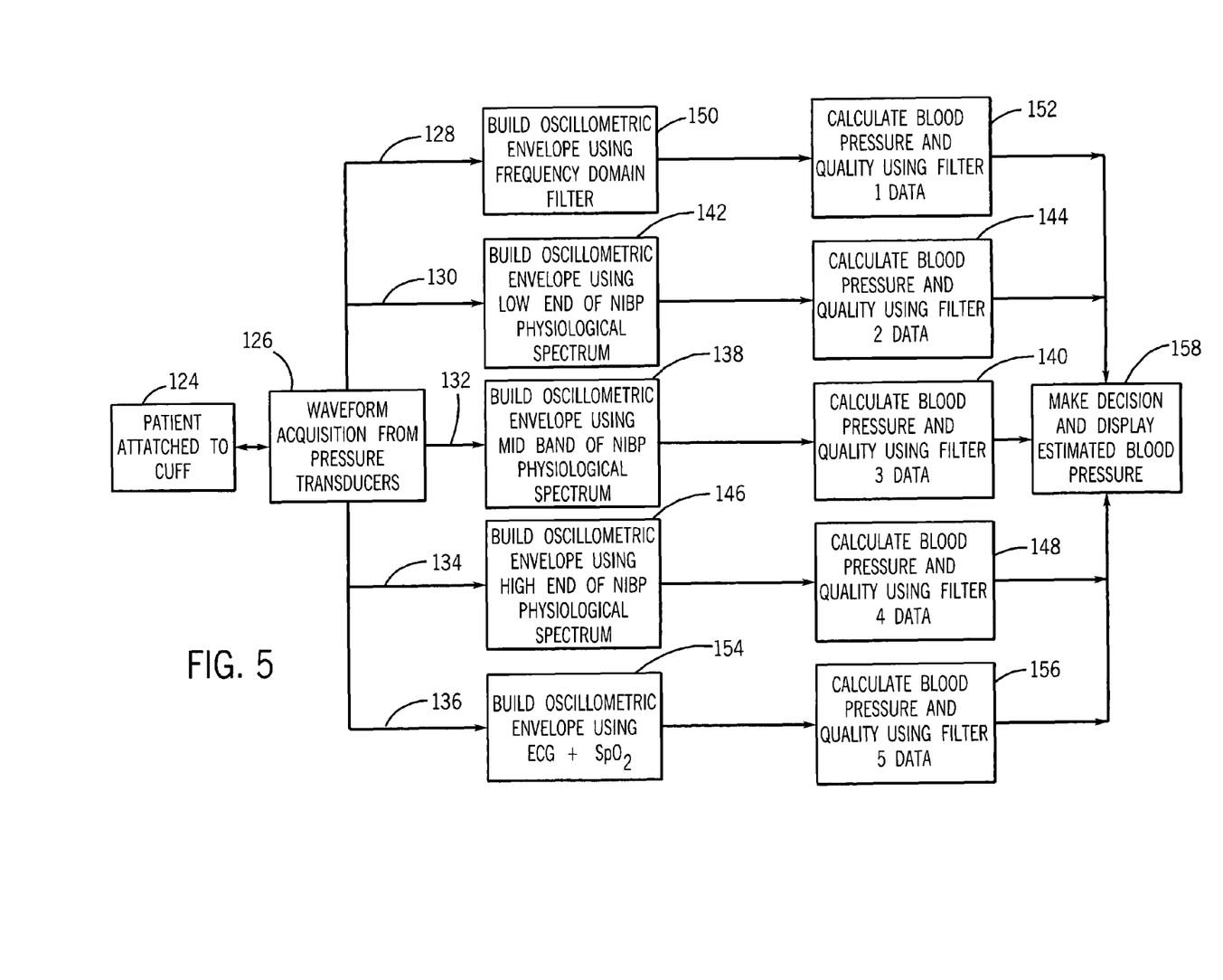
FIG. 5 is a high level flow chart showing the use of multiple channels, each including a different processing technique, to build an oscillometric waveform and the selection of the most relevant waveforms for the calculation of the patient's blood pressure.

FIG. 5 illustrates one embodiment for measuring and displaying the blood pressure of a patient 124 utilizing a conventional NIBP monitoring system to obtain pressure measurements. As illustrated in FIG. 5, the patient is attached to a blood pressure cuff which generates oscillometric data values from the pressure transducer, as shown in step 126. The oscillometric data values from the pressure transducers are fed to the central processor, which operates multiple, separate and distinct data processing channels 128, 130, 132, 134 and 136. In the embodiment of the invention illustrated in FIG. 5, each of the data processing channels 128-136 is separate and distinct from the other data processing channels and operates using a distinct processing technique to create its own oscillometric envelope. Although the embodiment of the invention shown in FIG. 5 is illustrated as having five separate data processing channels 128-136, it should be understood that the invention could be carried out with greater or fewer data processing channels while operating within the scope of the invention.

In the embodiment of the invention shown in FIG. 5 and as a specific example for a single channel, the data processing channel 132 creates an oscillometric envelope using a band pass filter having a mid-band (as opposed to a low-band or a high-band) within the usual physiological oscillometric frequency range, as illustrated in step 138. As a further illustrative detail, the pass band for the filter utilized in step 138 may have a lower cutoff point near 0.5 Hz and an upper cutoff point near 7.2 Hz. After the oscillometric envelope has been created in step 138, the central processor calculates blood pressure in step 140.

In addition to calculating blood pressure in step 140, the central processor also utilizes a quality algorithm to determine if the oscillometric envelope has a general bell-shape. An example of a quality calculation is set forth in U.S. Pat. No. 6,358,213, the disclosure of which is incorporated herein by reference. In accordance with the '213 patent, the central processor generates a quality value that relates the oscillometric envelope to a generally bell-shaped curve when doing the curve fitting techniques. The quality value assigned to the oscillometric envelope is such that each oscillometric envelope is rated between 0 and 100, where 100 represents the highest quality.

At the same time the data processing is occurring in channel 132, a similar data processing technique is taking place in step 142. In step 142, the oscillometric data values from the pressure transducer are used to create a second oscillometric envelope utilizing a low-band filter. Unlike the mid-band filter used in step 138, the low-band filter may be selected to have a pass band from 0.5 Hz to 3 Hz. Once the oscillometric envelope is created in step 142 using the lower end of the NIBP measurement spectrum, the blood pressure and quality are again calculated in step 142. As described above, the quality of the oscillometric envelope may be rated between 0 and 100 to give a comparative quality value of the oscillometric envelope from the data channel 130 relative to the data channel 132.

Data channel 134 includes a high-band filter that builds an oscillometric envelope utilizing a pass band from 3 Hz to 7.2 Hz, as illustrated in step 146. The oscillometric envelope created in step 146 is then used in step 148 to calculate a blood pressure and a quality measurement value. Once again, the quality value may range between 0 and 100 such that the quality of the blood pressure measurement in step 148 can be compared to the two other data channels 130 and 132.

In addition to the band pass filters shown in each of the data processing channels 130-134, the system may also include other data processing techniques to construct an oscillometric envelope. As an example, step 150 includes a frequency domain filter that processes the oscillometric data values. This filter picks specific and multiple frequency components (magnitude and phase) to construct multiple envelopes as output. The output of the frequency domain filter in step 150 is used to calculate the blood pressure and generate a quality value in step 152. Once again, the quality value calculated in step 152 is similar to the quality value calculated in data channels 130-134.

In data channel 136, another processing technique taking advantage of the timing relationship of the oscillations with respect to the ECG and SPO2 measurements is utilized. For example, the ECG information could be used to control opening a window of a particular width when the blood pressure oscillation is expected. In step 154, the oscillometric envelope is calculated using the ECG and SPO2 measurements and the oscillometric envelope is utilized to calculate a blood pressure and quality value, as shown in step 156.

Although various types of processing techniques are shown in the embodiment of the invention shown in FIG. 5, other processing techniques are contemplated as being within the scope of the present invention. As an example, it is contemplated that the oscillometric envelopes can be calculated using adaptive filtering by configuring the filter properties based on the heart rate or peak match filtering and template matching. In any case, the data processing channel generates a calculated blood pressure and quality measurement that can be utilized to compare the quality of the blood pressure estimates generated by each of the plurality of data processing channels 128-136. It should also be noted that the quality value can be calculated in a number of different ways. Rather than comparing the envelope points to a bell shaped curve, the quality could be based on the oscillometric pulse size variation found at each step of the deflation period. As another example, the quality could be based on estimates of the size of the noise present as compared to the size of the signal. Furthermore, the quality itself may not alone be sufficient to absolutely identify a good blood pressure or oscillometric envelope; for this reason the distance between the blood pressures from the different channels can enhance the decision making process as will be described below.

After the blood pressure and quality values have been calculated for each of the data processing channels 128-136, this information is compared within the central processor and a decision is made in step 158 as to the estimated blood pressure to be displayed by the NIBP monitoring system. The decision as to which one or combination of the data processing channels to utilize to display an estimated blood pressure can be determined using various different types of selection techniques. Each of the techniques allows the system to utilize the plurality of blood pressure estimates and quality values to generate an estimated blood pressure. Since each of the data processing channels 128-136 utilizes a different type of processing technique, the various types of processing techniques will more effectively eliminate the presence of noise and/or artifacts within the oscillometric method. If a good decision can be made in choosing or combining the information from each of the channels, the use of multiple data processing channels gives a better chance of providing a more accurate reading. However, a good method must be defined for reducing this multi-channel information to a single set of blood pressure values and will also now be described.

In a first contemplated method of determining the most appropriate blood pressure estimate to display, the microprocessor compares the quality values generated by each of the data processing channels in steps 140, 144, 148, 152 and 156. In a simple selection process, the microprocessor may choose the data processing channel having the highest quality value and simply display the calculated blood pressure determined by that data processing channel. In this most direct embodiment, each of the data processing channels 128-136 would be given equal weight and the data processing channel that generates the highest quality value would be the calculated blood pressure displayed in step 158.

Figure 7:
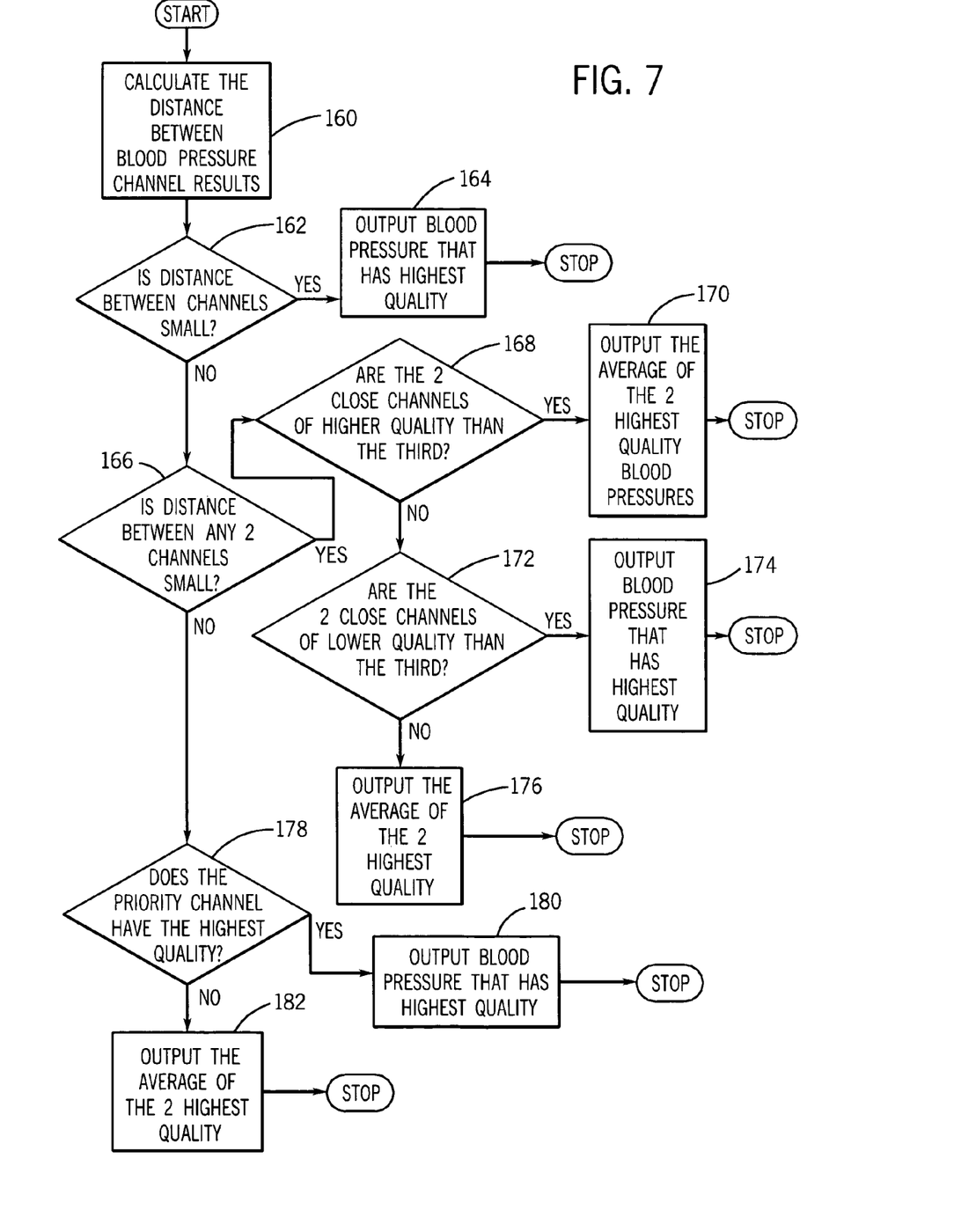
FIG. 7 is a flow chart showing how the various oscillometric waveforms calculated using different processing techniques can be correlated and combined to generate a blood pressure display.

Although utilizing a single blood pressure estimate from one of the plurality of data processing channels is an improvement over the prior art that relied upon only a single processing technique, it is contemplated that the results of the multiple data processing channels 128-136 could also be combined in a more sophisticated way to generate a resulting blood pressure estimate. Referring now to FIG. 7, thereshown is another embodiment of a method for combining and/or comparing the estimates from the data processing channels.

In the method shown in FIG. 7, the microprocessor initially calculates the distance between each of the data processing channels and each of the other data processing channels shown in FIG. 5. Specifically, the distance calculated in step 160 can be defined as:

$$SQRT((Systolic\ 1-Systolic\ 2)^2+(Diastolic\ 1-Diastolic\ 2)^2+(MAP\ 1-MAP\ 2)^2)$$

Note, however, that the distance between data channels can be computed in a number of different ways. For example, the envelope data could be compared directly rather than first finding the resultant blood pressure values. One way of comparing envelopes more directly would include an estimated sum squared difference of the envelope data itself. Other direct of methods for envelope distance calculations of practical use can be easily defined.

In step 160, the distance is calculated between each data processing channel and each of the other data processing channels to create a series of distance measurements. In step 162, the microprocessor determines whether the distance between all of the data processing channels are relatively small. By using these distance values the algorithm can further enhance the decision process for computing the best blood pressure for output. If the differences between the distance values for all the channels is small, for example the distances are less than 3 mmHg, then each of the data processing channels has returned a very similar result, indicating the presence of very little noise or artifact. If the difference is small, as determined in step 162, the central processor outputs the blood pressure that has the highest quality value, as indicated by step 164. Once again, the quality value for each of the blood pressure estimates can be calculated utilizing the method described in the '213 patent set forth above.

However, if the central processor procedure determines in step 162 that the distances between the channels is not small, the system should then determine the output blood pressure estimation in a more sophisticated way taking the distance measurement into account. In what follows it will be assumed, purely as a means of showing an example, that there are three channels. If the distance between any two of the plurality of channels is small, as shown in step 166 then the quality of these two channels are compared to a third channel in step 168. If both the quality values for the two channels that were found to be close to each other in step 166 are higher in quality than the third channel, the central processor outputs the average of the two close, high quality channels in step 170. Note that in making these decisions, thresholds can be easily established for whether a quality is high or distances are close.

However, if both the two close channels are not of higher quality than the third channel, as determined in step 168, the system then determines whether the two close channels are both of lower quality than the third channel in step 172. If the system determines in step 172 that the third channel has a higher quality value than either of the two close channels, the system outputs the estimated blood pressure having the highest quality in step 174. Thus, although the two channels may be close to each other, if the two channels are both of lower quality than a third channel, the system outputs the channel having the highest quality in step 174.

If the two close channels are not both of lower quality than the third channel, the system then outputs the average of the two highest quality channels in step 176. In step 176, the system determines that although the two close channels are near each other, the system averages the two highest quality data channels in step 176, deciding at this point that the distance information will not enhance the accuracy of the output blood pressure.

If the system determines back in step 166 that the distance between any two channels is not small, the system then determines whether any of the data processing channels has been designated as a priority channel. In accordance with the present invention, the system can designate any one of the data processing channels as the priority channel. Typically, one or more of the data processing channels can be considered more important or more accurate than the other channels. As an example, data processing channel 132 includes a band pass filter having upper and lower limits of 0.5 Hz and 7.2 Hz. These upper and lower limits have generally been found to be the most reliable and accurate in processing oscillometric data and, as such, will typically be designated as the priority channel. Thus, whenever the multiple data processing channels do not generate two blood pressure estimates having a small distance between them, the system will default to utilizing the priority channel if the priority channel has the highest quality, as shown in step 178.

If the system determines in step 178 that the priority channel has the highest quality, the blood pressure will be output from that channel, as shown in step 180. However, if the system determines that the priority channel does not have the highest quality, the system will output the average of the two highest quality data processing channels as illustrated in step 182.

In summary, as the decision tree embodied by FIG. 7 illustrates, the system of the present invention utilizes multiple data processing channels that each generate a blood pressure estimate and a quality value based upon the oscillometric data values received from an NIBP monitoring system. Each of the data processing channels includes a separate and independent processing technique that creates an oscillometric envelope. Based upon the determined oscillometric envelope, the central processor generates a blood pressure estimate and quality value for the oscillometric data values. Once each of the data processing channels has created the blood pressure and quality values, the central processor can make decisions as to which of the blood pressure estimates to display based upon numerous possible variables, such as the distance between the various blood pressure measurements and the quality value. In either case, the central processor can select one or more of the blood pressure estimates from the multiple data processing channels, which reduces the effect noise and artifacts have on the calculation of the blood pressure.

Figure 6:
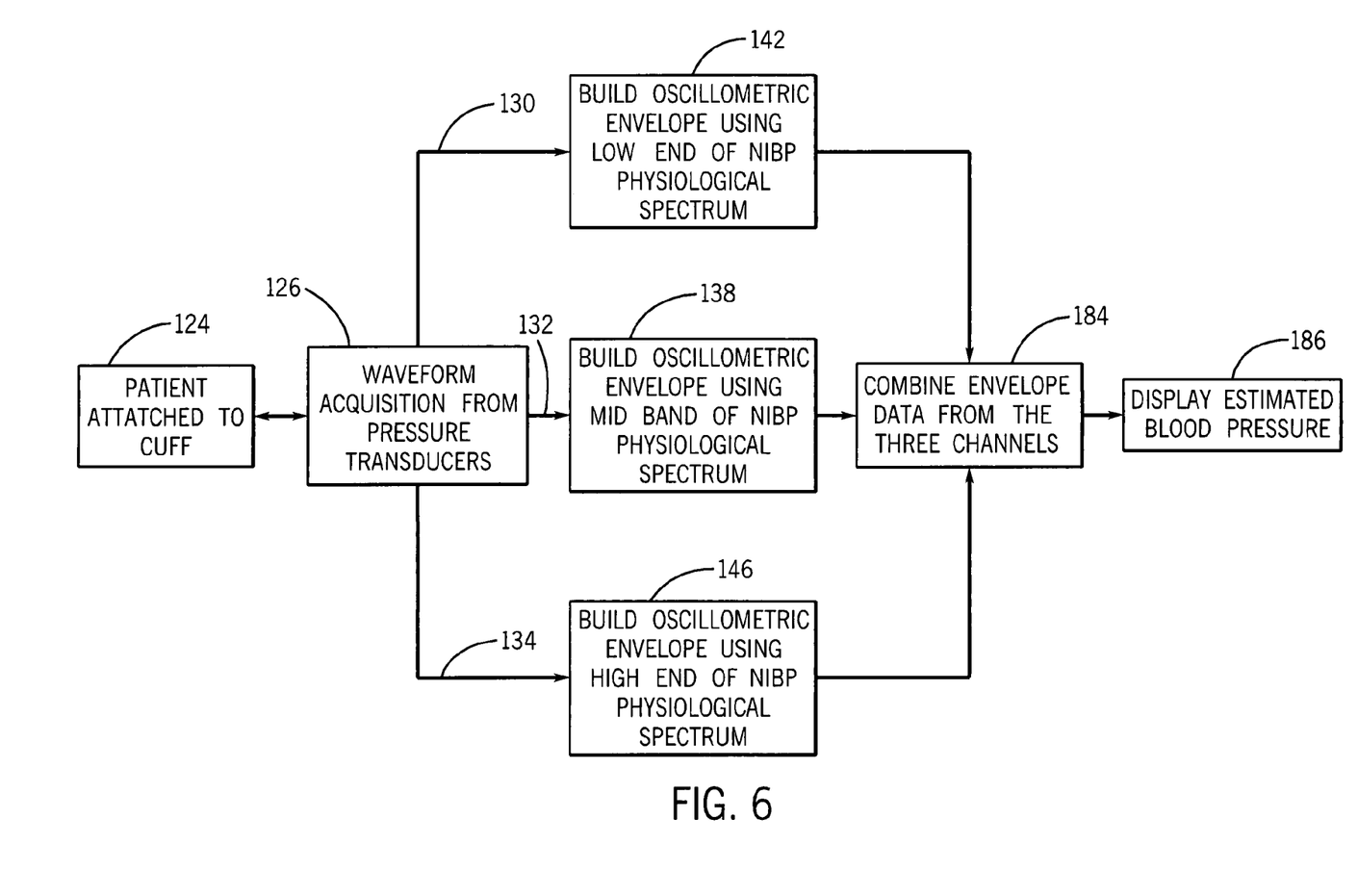
FIG. 6 is a flow chart similar to FIG. 5 illustrating the use of a plurality of different processing techniques to generate an oscillometric envelope where the oscillometric envelopes are combined to calculate a single blood pressure estimate.

Alternatively, rather than use a decision tree based on quality and distance to choose or combine the various channels, the oscillometric data can be combined in a more fundamental way. In the processing method and system shown in FIG. 5, each of the data processing channels 128-136 calculates a blood pressure and quality and the central processor decides which of these estimates to utilize in displaying the estimated blood pressure. In the alternative embodiment shown in FIG. 6, each of the data processing channels 130-134 builds an oscillometric envelope utilizing a different processing technique. However, in each data processing channel, the blood pressure and quality for the oscillometric envelope are not calculated as was the case in FIG. 5. Instead, the oscillometric envelope from steps 138, 142 and 146 are combined in step 184. The process of combination requires that the envelope data from each channel be scaled so that the maximum oscillation size for each envelope is the same or normalized. The combined envelope data from the three channels 130, 132 and 134 is then used to do the calculation of the blood pressure estimate in step 186. The embodiment of the invention shown in FIG. 6 thus combines three separate data processing techniques to generate a single oscillometric envelope in step 184, which is then used to calculate the output blood pressure displayed in step 186. The method of combining the envelope data from the three channels, as shown in step 184, is described in greater detail in FIG. 8.

Figure 8:
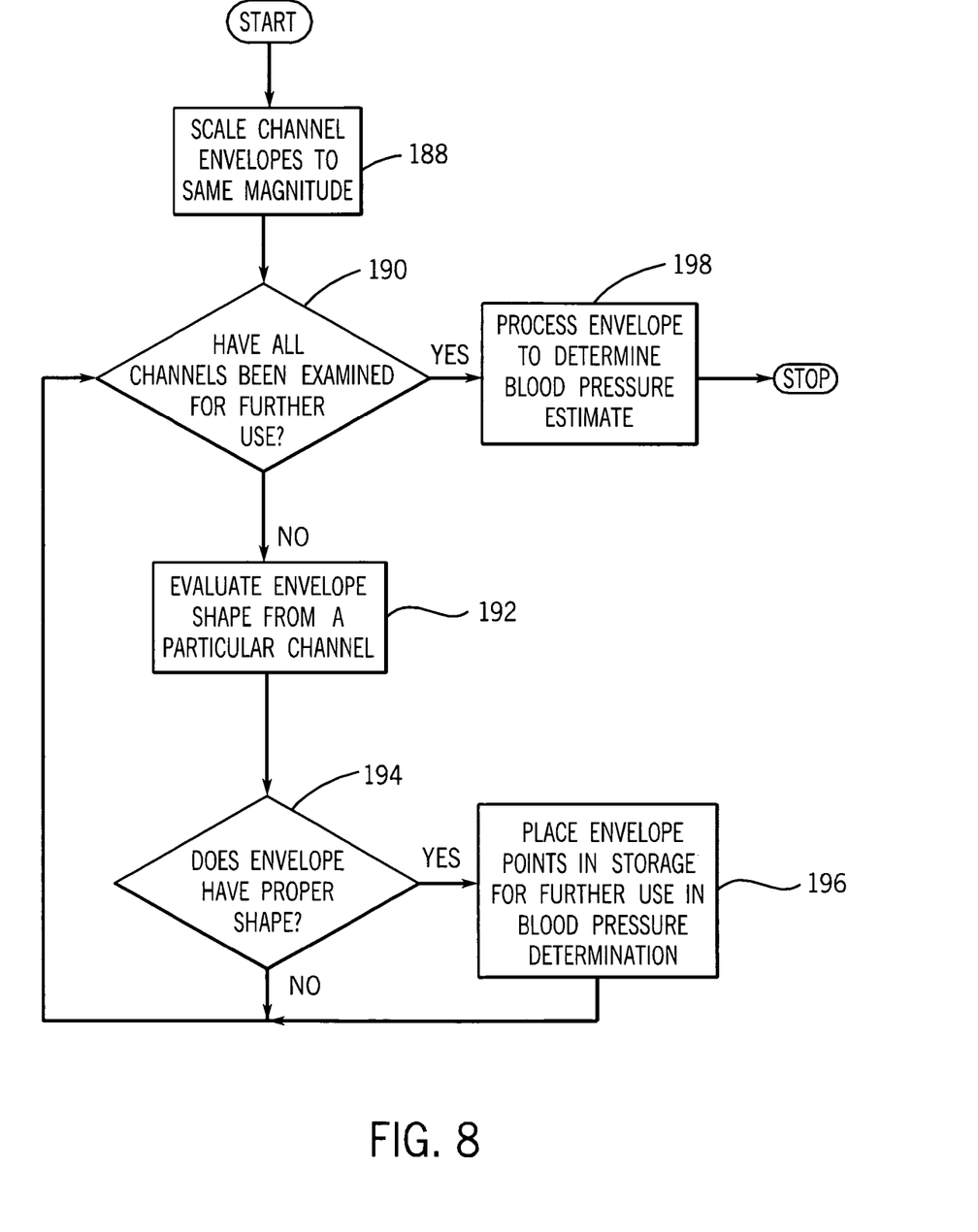
FIG. 8 is a flow chart illustrating the steps required to combine the oscillometric envelopes from multiple channels to generate a single blood pressure measurement.

As shown in FIG. 8, the oscillometric envelopes received from each of the data processing channels are initially scaled to the same magnitude as shown in step 188. Once the oscillometric envelope from each data channel is scaled to the same magnitude, the system determines whether or not the channels have been examined for further use in step 190. This is accomplished by evaluating the oscillometric envelope shape for the data coming from each channel in step 192. If the system determines that the oscillometric envelope has the proper shape, as shown in step 194, the envelope points are placed in the storage for further use in the calculation of the blood pressure, as shown in step 196. If the envelope does not have the proper shape, the system returns to step 190 and determines whether all of the channels have been examined for use. The steps 190-194 are completed for each of the data processing channels.

Once the system determines that all of the channels have been examined and the acceptable envelope data points are stored for further use, the system then treats this data as an overall oscillometric envelope in step 198. The overall oscillometric envelope created in step 198 utilizes the data points from the chosen oscillometric envelopes measured from each data processing channel. Thus, the overall oscillometric envelope calculated in step 198 and generally done by a curve fitting technique utilizes the data found from of each of the data channels, thereby reducing and/or eliminating the effect of of artifacts and noise present during the measurement procedure.

As described above, the system and method of the present invention utilizes multiple signal processing techniques on the oscillometric data values received from the pressure transducer of an NIBP monitoring system. The multiple data processing techniques are carried out in parallel and the results from the data processing techniques can be compared to determine which technique generated the oscillometric envelope having the highest quality. Alternatively, the oscillometric envelopes from the multiple data processing channels each using a different signal processing technique can be combined to construct an aggregate oscillometric envelope used to estimate the blood pressure for the patient. In the above description, various data processing techniques have been described for processing the oscillometric data values from the pressure transducer of the NIBP monitoring system. However, it is contemplated by the inventors that various other data processing techniques not specifically set forth above could be utilized while operating within the scope of the invention. Further, it is also contemplated by the inventors that different types of techniques for combining the information from the data processing channels can be utilized while operating within the scope of the present invention.

Various alternatives and embodiments are contemplated as being within the scope of the following claims particularly pointing out and distinctly claiming the subject matter regarded as the invention.

What is claimed is:

1. A method of measuring and displaying the blood pressure of a patient using a non-invasive blood pressure (NIBP) monitor having an inflatable and deflatable blood pressure cuff, a central processor, and a pressure transducer, the method comprising the steps of:

obtaining a plurality of oscillometric data values from the pressure transducer;

processing the oscillometric data values with the central processor that uses a first processing technique to construct a first oscillometric envelope;

processing the oscillometric data values with the central processor that uses a second processing technique separate from the first processing technique to construct a second oscillometric envelope;

determining with the central processor a signal quality value for the first and second oscillometric envelopes with the central processor;

calculating, with the central processor, the blood pressure from the first and second oscillometric envelopes based on the signal quality value; and displaying the calculated blood pressure.

2. The method of claim 1 wherein the step of determining the signal quality value for the first and second oscillometric envelopes includes comparing the first and second oscillometric envelopes to a predetermined, generally smooth bell-shape.

3. The method of claim 1 wherein in the first processing technique includes passing the oscillometric data values through a first bandpass filter and the second processing technique includes passing the data values through a second, different bandpass filter.

4. The method of claim 3 wherein the first bandpass filter has a pass range of between approximately 0.5 Hz to 3.0 Hz and the second bandpass filter has a pass range between 0.5 Hz and 7.2 Hz.

5. The method of claim 1 wherein the step of determining the blood pressure includes selecting the first or second oscillometric envelope having the highest signal quality value.

6. The method of claim 1 wherein the step of calculating the blood pressure includes combining the first oscillometric envelope and the second oscillometric envelope.

7. The method of claim 1 further comprising the steps of:
processing the oscillometric data value with the central processor that uses a third processing technique to construct a third oscillometric envelope;
determining with the central processor, a signal quality value for the third oscillometric envelope;
calculating with the central processor the blood pressure from the first, second and third oscillometric envelopes based on the signal quality value.

8. The method of claim 7 wherein the third processing technique includes passing the oscillometric data values through a third bandpass filter that is different from both the first and second bandpass filters.

9. The method of claim 8 wherein the third bandpass filter has a pass range between 3.0 Hz and 7.2 Hz.

10. The method of claim 7 further comprising the steps of:
calculating the systolic pressure, MAP and diastolic pressure for each of the first, second and third oscillometric envelopes;
determining the distance between the systolic, MAP and diastolic pressures for the first, second and third oscillometric envelopes; and
selecting the first, second or third oscillometric envelope based upon the calculated distance.

11. A method of measuring and displaying the blood pressure of a patient using a non-invasive blood pressure (NIBP) monitor having an inflatable and deflatable blood pressure cuff, a central processor, and a pressure transducer, the method comprising the steps of:
obtaining a plurality of oscillometric data values from the pressure transducer;
operating the central processor to:
process the oscillometric data values using a plurality of different processing techniques to construct an oscillometric envelope for each of the processing techniques; and
calculate the patient's blood pressure from the plurality of oscillometric envelopes; and
selectively displaying the calculated blood pressure.

12. The method of claim 11 wherein the step of calculating the patient's blood pressure includes:
comparing each of the plurality of oscillometric envelopes to a predetermined, general bell-shape;
assigning a quality value to each of the plurality of oscillometric envelopes based upon the conformance of the oscillometric envelope to the predetermined, general bell-shape;
selecting at least one of the blood pressure results based upon the quality value of each associated oscillometric envelope; and
displaying the patient's blood pressure that resulted from the selection process.

13. The method of claim 12 wherein the step of calculating the patient's blood pressure includes selecting the oscillometric envelope having the highest signal quality.

14. The method of claim 12 further comprising the steps of designating at least one of the plurality of different processing techniques as a priority technique, wherein the step of calculating the patient's blood pressure includes comparing the quality value of the oscillometric envelope from the priority technique to the quality value from the other processing techniques; and
displaying the blood pressure calculated from the oscillometric envelope of the priority technique when its quality value is above a threshold based on the quality values from the other processing techniques.

15. The method of claim 11 wherein the step of calculating the blood pressure comprises:
determining a systolic blood pressure, a diastolic blood pressure and a mean arterial pressure for each of the plurality of oscillometric envelopes;
determining the distance between the systolic blood pressure, diastolic blood pressure and mean arterial pressure for each of the plurality of oscillometric envelopes from the corresponding processing channels;
selecting the two channels having the smallest distance measurements between the systolic blood pressure, the diastolic blood pressure and the mean arterial pressure; and
averaging the results from the selected channels to determine the calculated blood pressure.

16. The method of claim 11 wherein the step of calculating the blood pressure comprises:
designating one of the plurality of processing techniques as a priority technique;
calculating a signal quality for each of the plurality of oscillometric envelopes by determining how close each of the oscillometric envelopes is to a general bell-shape;
assigning a quality value to each of the plurality of blood pressure results based upon the signal quality of the oscillometric waveform;
comparing the quality value of the priority waveform to the quality value of the plurality of oscillometric envelopes; and
calculating the blood pressure from the priority channel if the priority waveform quality value is above a threshold based on the quality values of the other processing channels.

17. The method of claim 11 wherein the step of calculating the blood pressure comprises:
   combining the plurality of oscillometric envelopes from the plurality of processing techniques to develop a aggregate oscillometric envelope;
   performing a curve fitting technique on the aggregate envelope; and
   calculating the patient's blood pressure based upon the aggregate envelope after curve fitting.

18. The method of claim 11 wherein the plurality of processing techniques includes providing multiple band pass filters each having a different pass band.

* * * * *